US009176041B2

United States Patent
Barraclough et al.

(10) Patent No.: US 9,176,041 B2
(45) Date of Patent: Nov. 3, 2015

(54) FILTRATION PARTICLE QUANTIFIER

(75) Inventors: Thomas G. Barraclough, Maynard, MA (US); Stephen D. Lawrence, Ayer, MA (US)

(73) Assignee: Spectro Scientific, Inc., Chelmsford, MA (US)

( * ) Notice: Subject to any disclaimer, the term of this patent is extended or adjusted under 35 U.S.C. 154(b) by 538 days.

(21) Appl. No.: 13/507,298

(22) Filed: Jun. 19, 2012

(65) Prior Publication Data

US 2013/0333449 A1    Dec. 19, 2013

(51) Int. Cl.
*G01N 15/06* (2006.01)
*G01N 33/28* (2006.01)
*G01N 15/00* (2006.01)

(52) U.S. Cl.
CPC ........ *G01N 15/0618* (2013.01); *G01N 33/2888* (2013.01); *G01N 2015/0053* (2013.01)

(58) Field of Classification Search
CPC ...................................................... G01N 15/06
See application file for complete search history.

(56) References Cited

U.S. PATENT DOCUMENTS

| | | | | |
|---|---|---|---|---|
| 3,591,003 | A * | 7/1971 | Cooper | 210/90 |
| 4,583,396 | A | 4/1986 | Hunt et al. | |
| 5,095,740 | A * | 3/1992 | Hodgson et al. | 73/61.73 |
| 5,266,495 | A * | 11/1993 | Lapidus | 436/63 |
| 5,385,043 | A | 1/1995 | Fitch et al. | |
| 5,932,795 | A * | 8/1999 | Koutrakis et al. | 73/28.01 |
| 6,230,551 | B1 | 5/2001 | Burniston | |
| 7,218,397 | B1 | 5/2007 | Bensch et al. | |
| 2005/0150841 | A1 * | 7/2005 | Ferguson | 210/741 |
| 2009/0001019 | A1 | 1/2009 | Frometa et al. | |
| 2009/0294385 | A1 * | 12/2009 | Tajima et al. | 210/808 |

FOREIGN PATENT DOCUMENTS

| | | |
|---|---|---|
| EP | 1 300 186 A1 | 4/2003 |
| GB | 2 315 869 A | 7/1996 |
| GB | 2 348 503 A | 10/2000 |
| WO | WO 84/00816 | 3/1984 |
| WO | WO 95/10765 | 4/1995 |

OTHER PUBLICATIONS

Written Opinion of the International Searching Authority for International Application No. PCT/US2013/25009 mailed Apr. 19, 2013 (eight (8) pages).
U.S. Appl. No. 13/374,937.
Spectro Inc., Monitoring Lubricant and Machine Condition Using Oil Analysis, www.spectroinc.com Jun. 17, 2010, 2 pages, vol. 2.5.

* cited by examiner

*Primary Examiner* — Hezron E Williams
*Assistant Examiner* — Mark A Shabman
(74) *Attorney, Agent, or Firm* — Iandiorio Teska & Coleman, LLP (57) ABSTRACT

A particle quantifier includes a filter with a predetermined number of pores of a first predetermined size, a pump, and a fluid path from the pump to the filter. A pressure sensor is responsive to fluid pressure in the fluid path, and a processing module is responsive to the pressure sensor. The pressure increase of a sample fluid in the fluid path is determined as it is pumped through the filter and particles in the fluid are trapped by the filter. This pressure increase is compared with calibration data and an estimate is made concerning the concentration of particles greater than a second predetermined size present in the sample.

40 Claims, 7 Drawing Sheets

FILTRATION PARTICLE QUANTIFIER

FIELD OF THE INVENTION

The invention relates to fluid analysis.

BACKGROUND OF THE INVENTION

Particles in fluids can be quantified in a number of ways. The number of particles present in an oil sample from a motor or engine greater than a certain size, for example, can be indicative of the condition of certain motor or engine components and/or indicative of impending failure.

Traditionally, ferrography analysis using optical microscopy is used to determine abnormal failure modes in machines based on visual inspection of large particles and their associated morphologies. This type of analysis can be time consuming and subjective because it requires an expert analyst. More recent direct imagining instruments have been developed to automatically quantify the size and distribution of wear particles and to also provide some indication of shape. One limitation of such devices is their inability to analyze highly viscous oils and very dark fluids without dilution. The resulting particle counts can often be skewed because of interference from additives, water, and dissolved gases.

U.S. Pat. No. 4,583,396, incorporated herein by this reference, teaches a by-pass contamination indicator for a hydraulic system. The system includes a barrier which, when blocked by particles, causes a pressure drop across the barrier to reach a certain value. By counting how long it takes to reach this pressure value, the general contaminate level (low, medium, high) can be determined. The total number of particles larger than the barrier pore size is said to be calculated based on the pore size, the number of pores, the flow rate, and pressure drop.

This system is adapted for addition to a hydraulic system; not for analyzing samples of fluid. Moreover, the emphasis of such a system is cleanliness control and keeping such a system clean and free of contamination to known limits is the primary goal. In a hydraulic system, the valves and actuators must be kept clean and free of debris to function properly. Light blocking and pore blockage technology has been designed around such clean systems.

In lubrication systems, benign wear particles are generated as a natural consequence of the mechanical operation of the machine being lubricated. A good example is a diesel engine. The extremities of the components in the cylinder and the piston acting between a hydrodynamic film of lubricant act as a stable wearing surface and particles are exfoliated as normal rubbing wear platelets. Existing light blocking and pore blockage technologies are not ideally suited for these applications without some degree of sample preparation.

SUMMARY OF THE INVENTION

In this invention, in one embodiment, engine oil and the like is analyzed in a system calibrated using different calibration samples each with a different concentration of particles greater than a given size. The result is a unique way of measuring particle counts across a wide range of lubricant oils and fluids with varying viscosities and particle loading distributions. The particle count is derived by measuring the pressure drop as oil is pushed through a filter system including a polycarbonate filter of a given pore size. The geometry of the filter aperture and filter pore density is designed in such a way that caking is kept to a minimum. Also, the addition of felt filter enables particle quantification even after the polycarbonate filter becomes caked. In this region of minimum filter caking, samples with different viscosities and particle distributions correlate to a unique calibration curve.

The result is the ability to give advanced warning of impending machine failures by reporting the size and quantity of wear particles and contaminates in lubricating oils. After an analysis in the particle quantifier of the invention, the particles can be stored and saved for further analysis based on particle deposition using x-ray and/or microscopy type analysis procedures.

The filtration methodology used results in an evenly deposited array of particles which can be elementally quantified using x-ray (e.g., xrf) analysis if desired. A real time particle count is used to insure that the particles are laid down perfectly and optimized for x-ray and microscopy analysis.

Featured is a particle quantifier comprising a filter system with at least a first filter having a predetermined number of pores of a predetermined size, a pump, and a fluid path from the pump to the filter system. A pressure sensor is responsive to fluid pressure in the fluid path and a processing module is responsive to the pressure sensor. The pressure increase of a sample fluid in the fluid path is determined as fluid is pumped through the filter system and particles in the fluid are trapped by the first filter. The determined pressure increase is compared with calibration data. Based on the calibration data, an estimate is made concerning the concentration of particles greater than a predetermined size present in the sample. Typically, the particle size is greater than the pore size.

One preferred particle quantifier further includes a removable cartridge for the filter wherein a membrane filter is disposed over a well housing a second filter in a filter holder. Typically, the fluid path includes a syringe, the pump includes a motor driven plunger received in the syringe, and a holder receives the syringe and is sealed with respect to the first filter. The pressure sensor is then disposed to measure an internal pressure of the holder.

The calibration data preferably includes the pressure increase of a plurality of calibration fluid samples each with a known concentration of particles of a known size driven by the pump through the filter system and a calibration curve is based on the pressure increase of a plurality of calibration fluid samples. The processing module is typically configured to determine first and second pressures at different times as the sample fluid is pumped through the filter.

The processing module is also preferably configured to control the pump, e.g., the speed of the pump. Then, the calibration data includes a first predetermined pressure and the processing module is configured to control and vary the speed of the pump so the sample fluid reaches a predetermined pressure at a certain speed and to thereafter to hold that speed constant. Also, the processing module is further configured to stop the pump if a predetermined maximum pressure is reached and to extrapolate a pressure increase for a predetermined volume of fluid pumped through the filter system after the pump is stopped.

There may be a second filter with a predetermined number of pores of a different size and the processing module can be configured, based on the calibration data, to now estimate the concentration of particles within a size range One particle quantifier features a removable filter cartridge including a membrane filter disposed over a well in a filter holder also including a felt filter. The filter membrane includes a predetermined number of pores of a first size. A syringe is placed in a holder sealed to the to the filter cartridge. A processing module determines the pressure increase of a sample fluid as it is pumped out of the syringe and through the membrane filter and particles in the fluid are trapped by the pores of the membrane filter.

Also featured is a particle quantification method comprising driving a sample fluid through a filter system with at least a first filter having a predetermined number of pores of a first predetermined size, and determining the pressure increase of the sample fluid as it is driven through the filter system. The determined pressure increase is compared with calibration data representing the pressure increase of a plurality of calibration fluid samples as they were also driven through one or more filters with the same or a similar predetermined number of pores of the first or a similar predetermined size. Based on the comparison, the method includes estimating the concentration of particles present in the sample greater than a second predetermined size equal to or greater than the first predetermined size.

The calibration data may include a first predetermined pressure and the sample fluid is driven to reach this first predetermined pressure in the fluid path. Driving preferably stops if a predetermined maximum pressure is reached. The method may include extrapolating the pressure increase for a predetermined volume of fluid pumped through the filter after driving stops.

The subject invention, however, in other embodiments, need not achieve all these objectives and the claims hereof should not be limited to structures or methods capable of achieving these objectives.

BRIEF DESCRIPTION OF SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
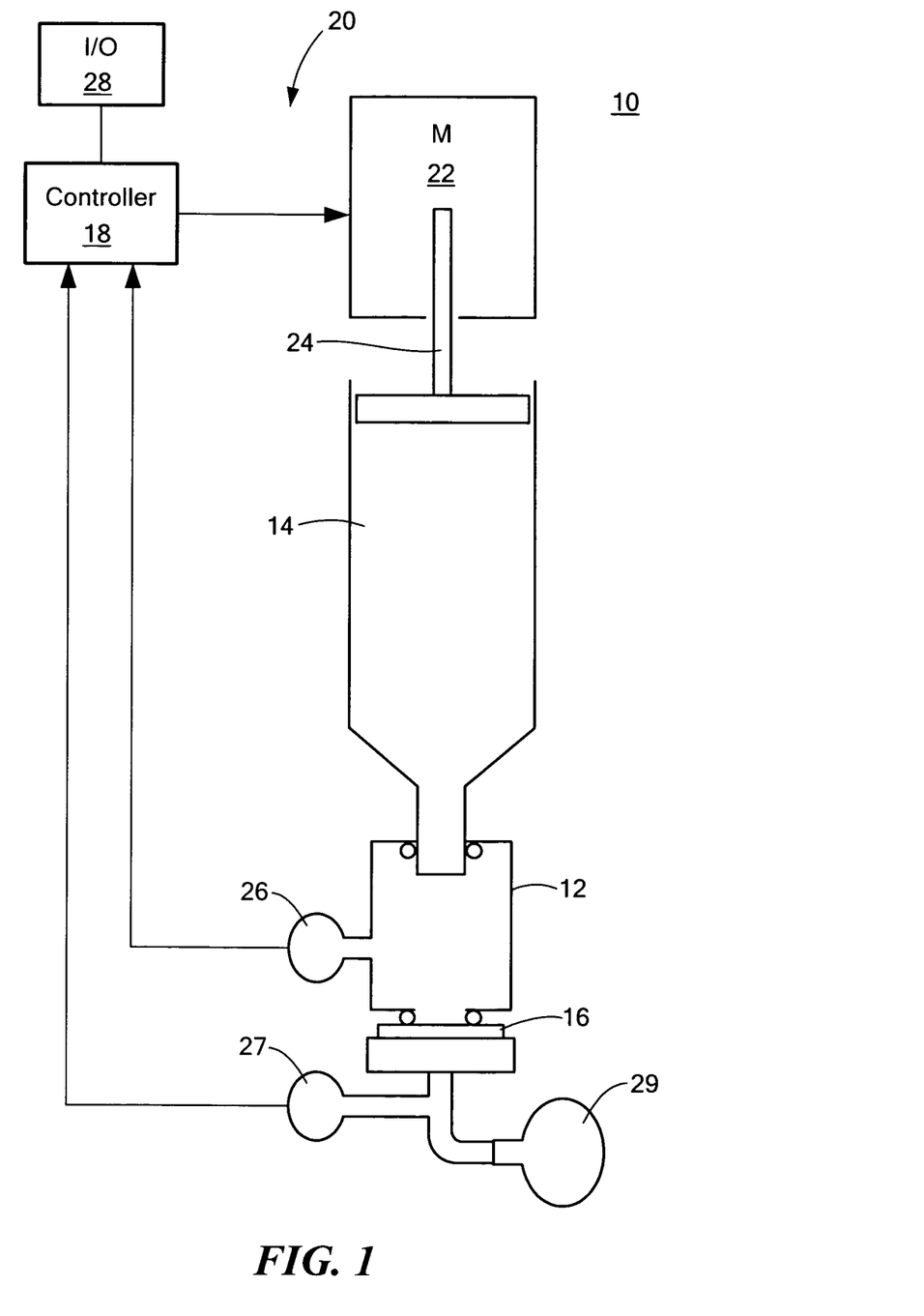
FIG. 1 is a schematic depiction showing the primary components associated with an example of a particle quantifier of the invention.

Portable particle quantifier 10, FIG. 1 includes, in one example, syringe holder 12 defining a sealed fluid path from the interior of syringe 14 to a filter held by cartridge 16. Syringe 14 is typically used to retrieve a 3 ml sample of engine oil or motor oil and is then placed in holder 12. Controller 18 or some other processing module (e.g., a microcontroller, a processor, a programmable logic circuit, a combination thereof, an application specific integrated circuit, or the like) controls a pump such as linear actuator 20 with variable speed motor 22 driving syringe plunger 24. Plunger 24 drives oil from syringe 14 through the filter held by cartridge 16.

Based on the pressure sensed by pressure transducer 26, controller 18 establishes the concentration of particles present in the oil sample greater than a predetermined size. By using a different filter cartridge, it is also possible to establish a concentration of particles greater than a second predetermined size and then a differential measurement between the small and large particles can be made in order to asses the condition of a machine, engine, or the like from whence the sample was taken.

In this way, the user retrieves an oil sample from a machine using the syringe and places the syringe in the holder of the quantifier and then the analysis is conducted automatically. After automatic quantification, the user can remove cartridge 16 and further study the oil sample particles deposited on the filter. The syringe can be cleaned and re-used or discarded.

Optional pressure transducer 27 can be used to detect when something is wrong with the oil drain system including nitrile bag 29 receiving oil which has passed through the filter.

Figure 2:
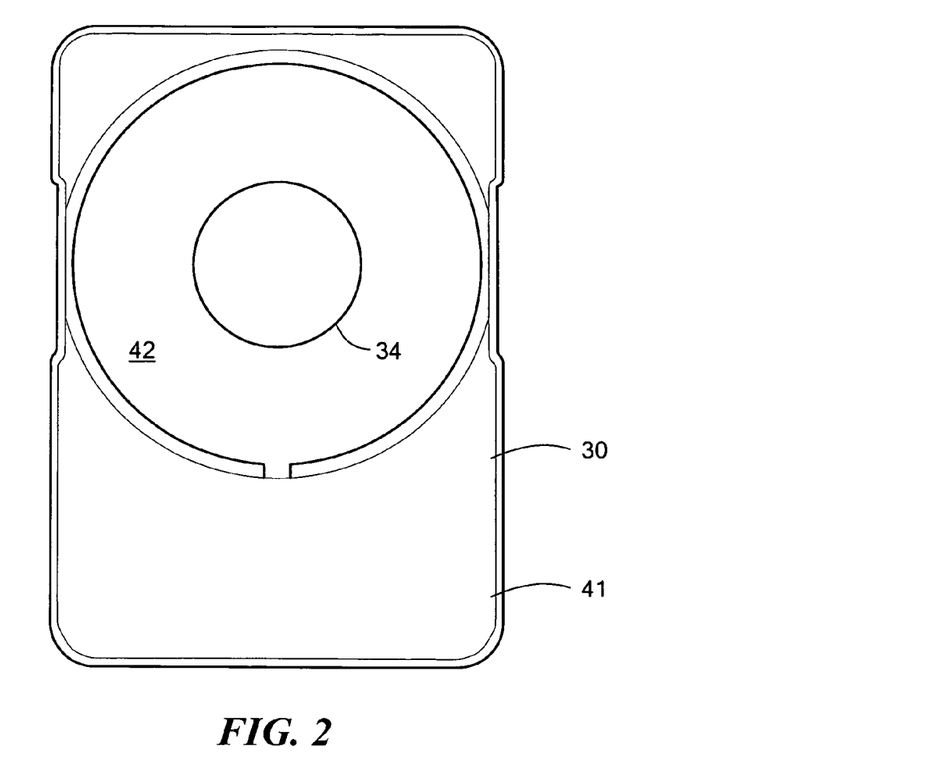
FIG. 2 is a schematic top view of an example of a filter cartridge in accordance with the invention.
Figure 3:
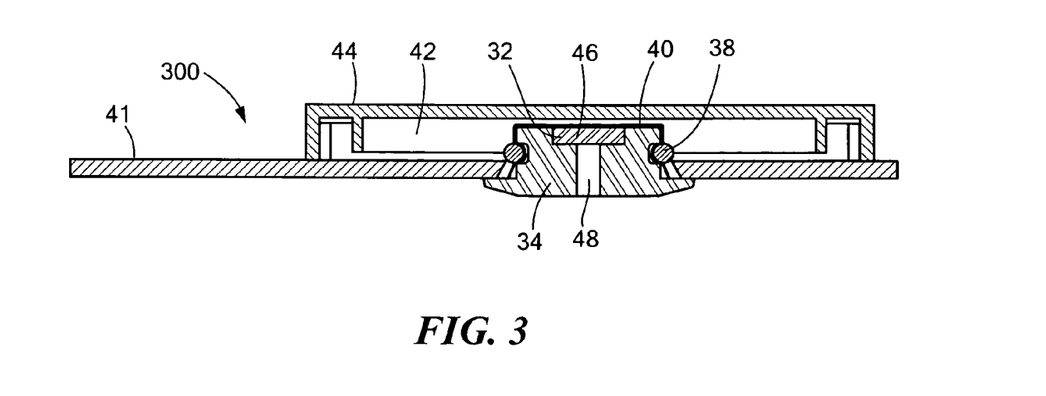
FIG. 3 is a schematic cross sectional view of a filter cartridge in accordance with an example of the invention.

FIGS. 2-3 show cartridge 30 preferably provided with the system. Cartridge 30 includes well 32 and filter holder 34 over which 0.005 inches thick filter membrane 40 is disposed and held in place via band 38. Filter holder 34 is typically snap-fit into plate 41 which features overflow well 32. Cartridge cover 44 may also be included in order to store a particular sample. In this particular example, felt material 46 fills well 32 and out flow port 48 is provided through filter holder 34 out of well 32 for sample fluid which has passed through filter 36.

Figure 4:
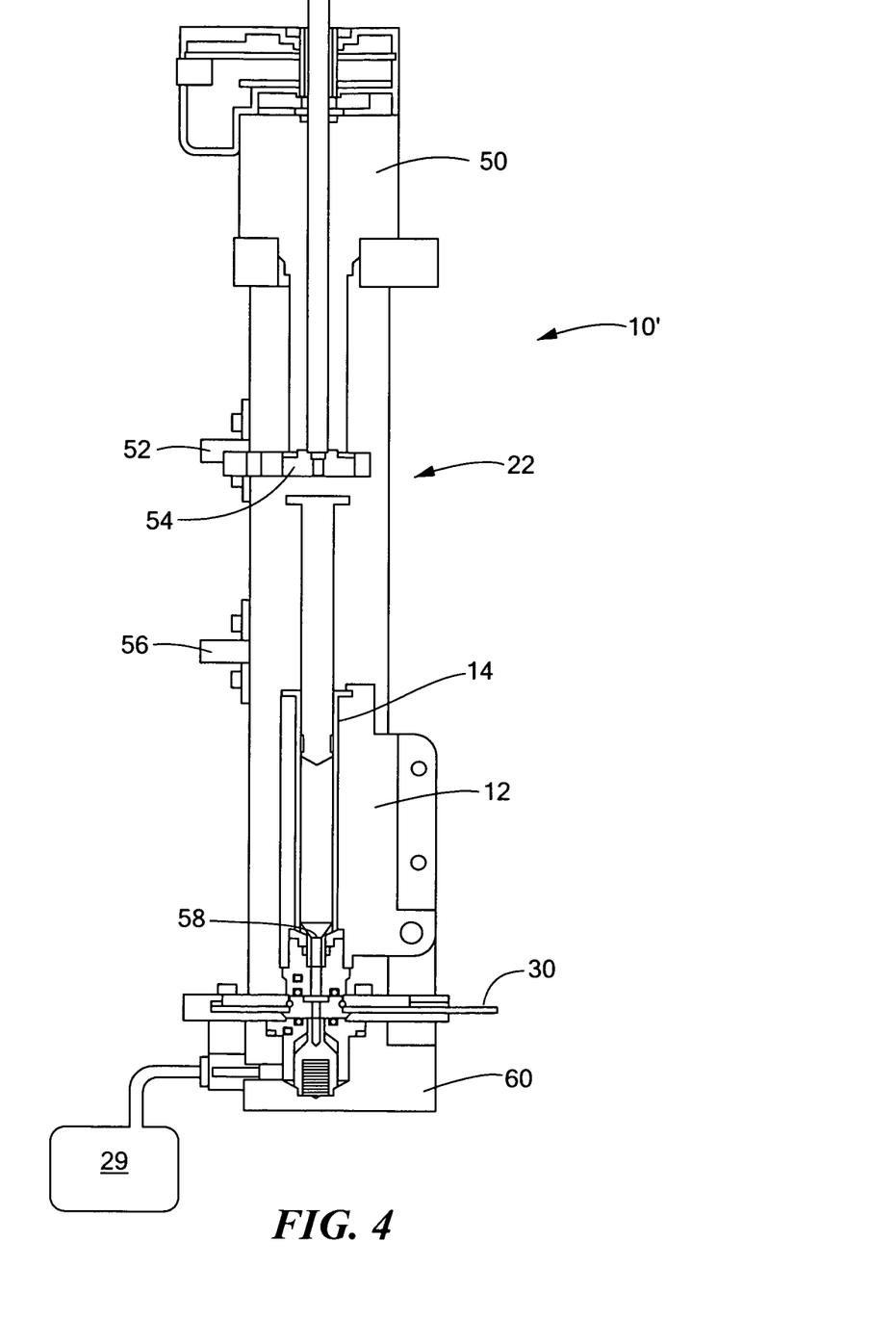
FIG. 4 is a schematic cross sectional view showing another example of a particle quantifier apparatus in accordance with examples of the subject invention.

Particulate cartridge 30 is placed as shown in FIG. 4 in quantifier 10. The syringe pump subsystem drives fluid through polycarbonate filter 36, FIG. 3, through felt filter 46, and into outlet 48 to be collected in a bladder.

FIG. 4 depicts several of the primary components associated with the typical quantifier including liner actuator 50, rear position sensor 52, syringe pusher 54, front position sensor 56, syringe 14, syringe holder 12, and syringe stop 58. Particulate cartridge 30 is shown in place below syringe 14. Below the cartridges is drain block 60 connected to bladder 29 for excess sample fluid exiting port 48, FIG. 3 of the particulate cartridge. Pressure transducers provide the input needed for particle counting. The feedback-based algorithm monitors these pressures and adjusts the pump motor speed as necessary to provide an accurate particle count for a wide range of viscosities. In most embodiments, the filter cartridge is sealed with respect to the syringe.

Controller 18, FIG. 1 is typically programmed as follows. During calibration, a filter with a known number of pores of a particular size is place in the quantifier and known calibration oil samples each with a known number of particles greater than a predetermined size are processed in the quantifier. In one example, three cartridges were used each with a polycarbonate filter having approximately 31,600 5 um pores. Three different calibration samples as follows were processed through there respective three cartridges:

TABLE 1

| CALIBRATION SAMPLE NO. | PARTICLES >4 um |
|---|---|
| 1 | 50,000 |
| 2 | 100,000 |
| 3 | 150,000 |

Figure 5:
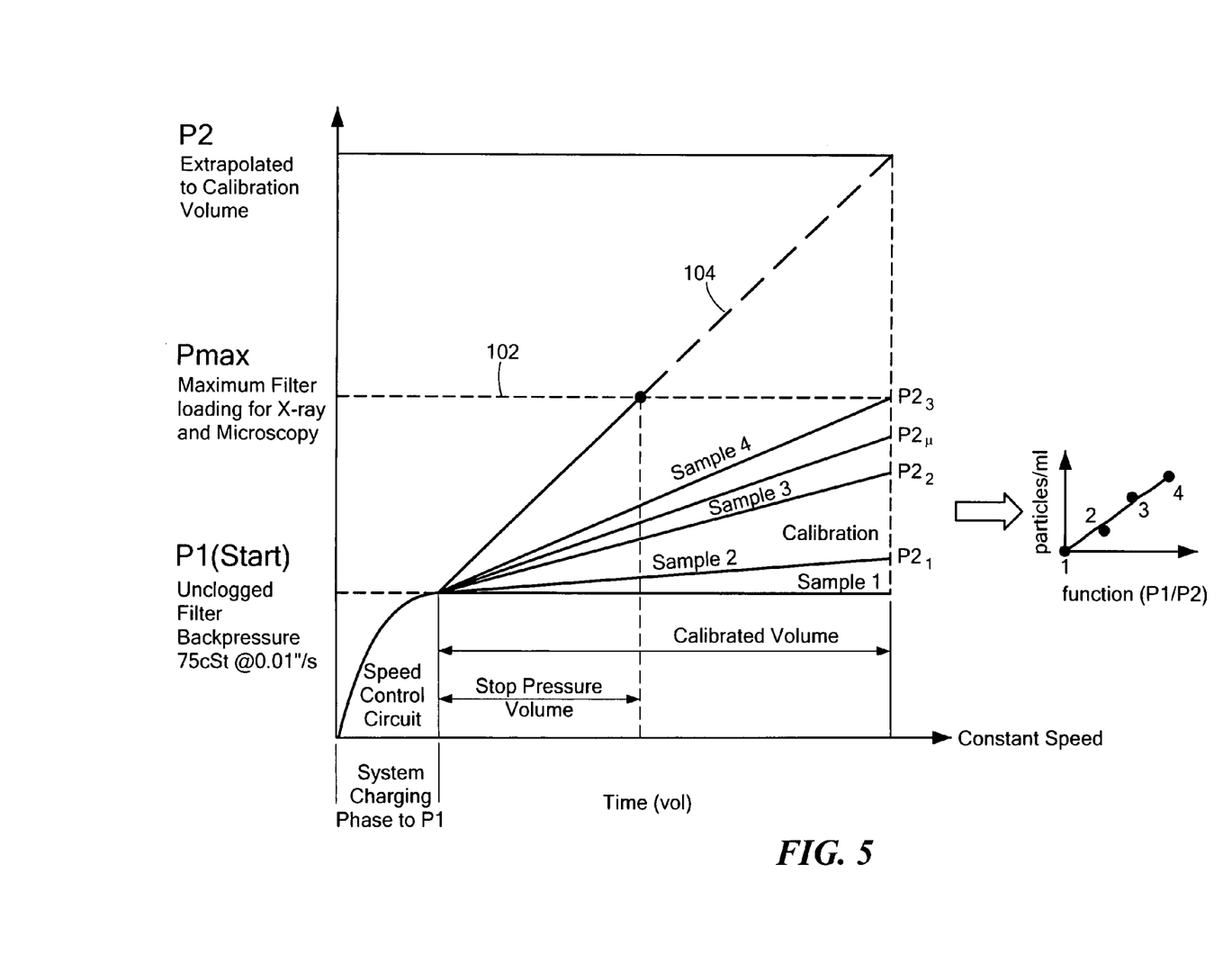
FIG. 5 is a graph showing pressure versus pumping time for three calibration samples and one unknown sample in accordance with aspects of the invention.
Figure 6:
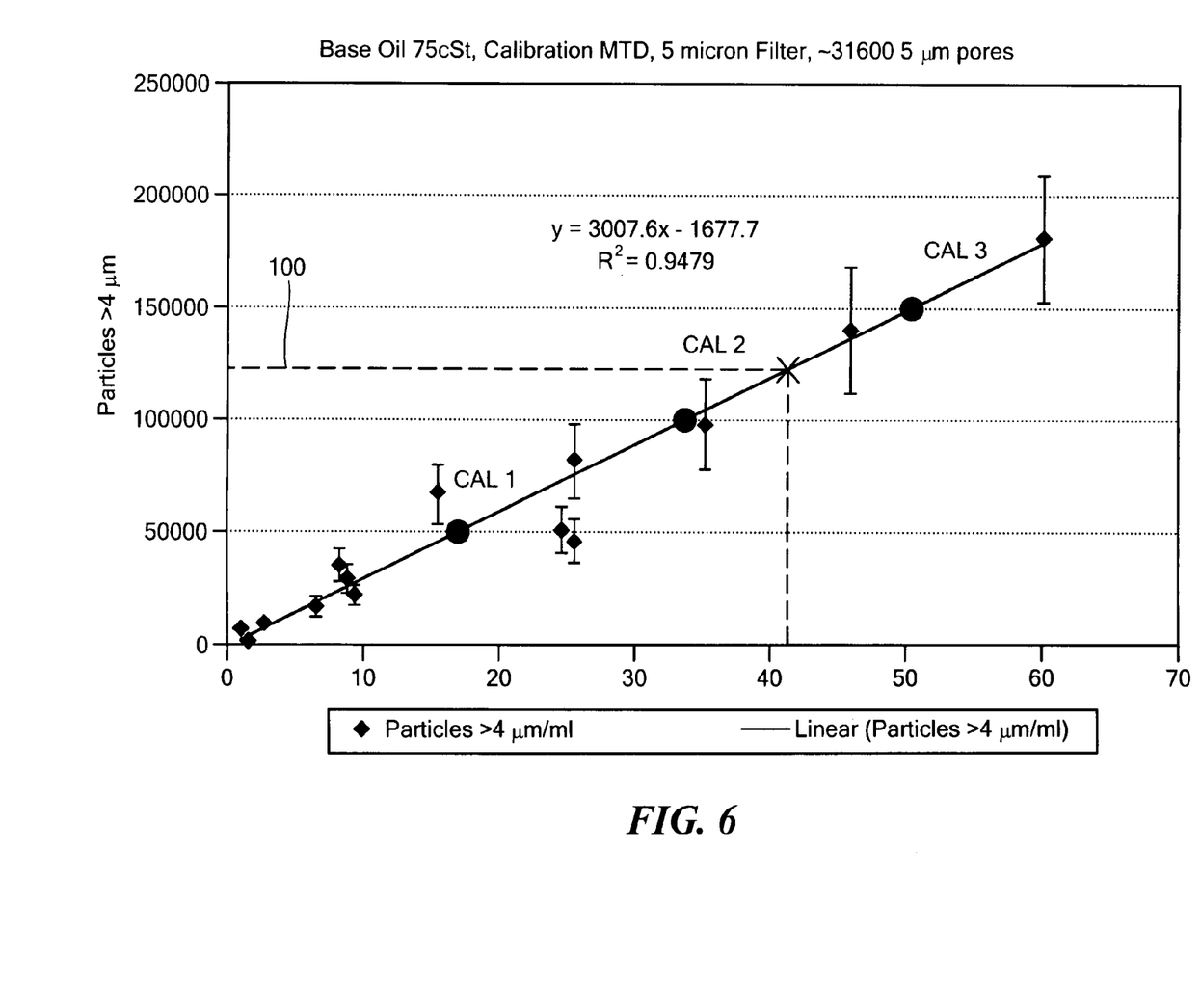
FIG. 6 is a calibration graph including calibration data used in conjunction with the invention.

The pressure rise was determined for each calibration sample after 3 ml of calibration fluid was pumped through the filter as shown at $P2_1$, $P2_2$, $P2_3$ in FIG. 5. Typically, many more calibration samples are run to increase the number of data points. Using this data, the linear graph of FIG. 6 is produced.

Now, 3 ml of oil with an unknown concentration of particles greater than 4 um is driven through another cartridge with a filter having 31,600 5 um pores. As particles in the fluid are trapped in the filter the pressure detected by sensor 26, FIG. 1 and read by controller 18 rises. After 3 ml of fluid are pumped through the filter, the pressure reaches $P2_u$. $P2_u$ was read and, based on the pressure level and the data of FIG. 6, the number of particles greater than 4 um in the unknown was estimated to be 125,000 as shown at 100 FIG. 6.

In more sophisticated systems, $P_1$, FIG. 5 is a starting pressure and all calibration and unknown samples reach $P_1$ before data is collected to account for different oil viscosities. The time it takes to reach $P_1$ for an unknown sample is recorded and the speed of the pump is controlled by controller 18, FIG. 1 for higher viscosity samples. So, for higher viscosity samples, the pump speed is lowered and, conversely, for lower viscosity samples the pump speed is increased. The calibration sample pump speed for calibration samples all at the same viscosities was 0.01 inches per second and $P_1$ was 9 psi.

In some cases, $P_2$ might not be reached before a maximum pressure is detected reflecting a maximum filter loading for x-ray and microscopy analysis (e.g., more than one layer of particles of layers on the filter). This maximum pressure $P_{max}$, FIG. 5 is determined as the pressure to give the optimum particle layer for a given volume of oil. The optimum particle layer was determined empirically through testing by increasing particles until no increase in signal was obtained. So, if a sample reaches the maximum pressure $P_{max}$ before 3 mls of fluid is pumped through the filter, the pump is stopped and $P_2$ is extrapolated as shown at 104. In this example, a linear extrapolation is shown. The actual rise in particles will be slightly exponential so a polynomial extrapolation can also be used to increase accuracy. The volume pumped, which is a function of the time it takes to reach $P_{max}$, is also recorded by controller 18, so later systems and/or analysts are aware of the non-standard (e.g., less than 3 mls) volume.

Note that by using another filter (e.g., 31,600 pores 15 um in diameter) and by running known calibration samples through this filter, a range of particle sizes can be estimated for a given sample after running the sample through both filters. Thus, for example, the number of particles between 4-14 um can be estimated. Differential measurements between small and large particles can be important in assessing the condition of a machine because large particles are typically present in an abnormal wear mode. It is preferred that the filter pore size (e.g., 5 um) be slightly larger than the estimated concentration particle size (e.g., 4 um) for better fit of the calibration data.

In one particular example, the pressure increase of 75 cSt oil with various concentrations of medium test dust (MDT) particles was recorded over a given volume for a constant pump speed of 0.01 inches per second. The ratio of the starting ($P_1$) pressure to the ending pressure $P_2$ for a given volume of oil pumped became the basis of the calibration.

$$\frac{P_1}{P_2}(-100) + 100 \tag{1}$$

yields a linear graph easier to understand. The particle concentrations were determined using a different type of technology, for example, a direct imaging particle counter.

The filter geometry and the flow of fluid follows Poiseuilles Law:

$$\Delta P = \frac{8 \mu L Q}{\pi r^4}. \tag{2}$$

In order to use a generic calibration curve for a wide variety of viscosities and particle counts, the forces acting on the particles in the filter must mimic the forces acting on the particles in the calibration. Controller 18, FIG. 1 implements a control circuit designed for different viscosity oils to reproduce the natural charging pressure of the syringe for the 75 cSt calibration oil. The initial charging pressure $P_1$ for the 75 cSt base oil calibrations at 0.01 inches per second is 9 psi. This pressure is reproduced for all the oils in the devices range (10 cSt-350 cSt) by controlling the speed of the pump motor until $P_1$ is reached and then that speed is held constant for the remainder of the test. The filter is designed to organize particles in a way for further testing with microscopy, ferrography, and x-ray type systems. The filter allows storage of the particles removed from the sample for further analysis at a later time. The size of the particles measured can be adjusted by using different pore sizes in the polycarbonate filter. An unknown oil was then analyzed and the syringe pump drive was driven to the initial pressure $P_1$ where the speed was then controlled until 3 ml of fluid was pumped or the maximum pressure was reached. $P_1$ and $P_2$ were recorded as well as the volume of oil consumed at $P_2$. If necessary, a linear or polynomial extrapolation is performed to derive the final true pressure $P_2$ when the maximum pressure is reached before the calibrated volume is filtered. Particle count is then estimated by inputting the $P_1$ and $P_2$ values into the master calibration equation.

Figure 7:
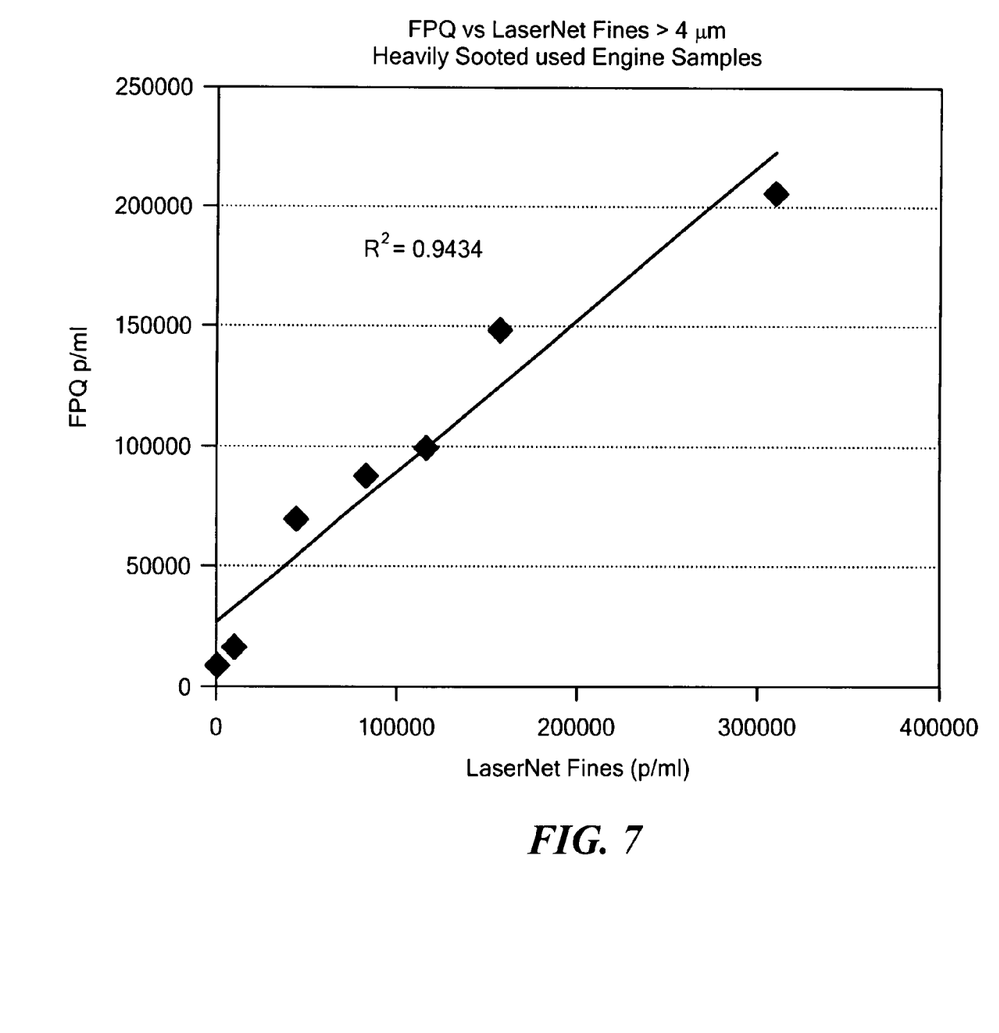
FIG. 7 is a graph of the method of the invention correlated with other particle quantifier technologies.

Samples were analyzed and a correlation was formed between this method and a calibrated direct imaging particle count system as shown in FIG. 7 for a series of heavily sooted used diesel engine samples. The correlation was 94%. Note that most of these samples were too dark for the direct imaging system and required dilution before a particle count was able to be reported.

Figure 8:
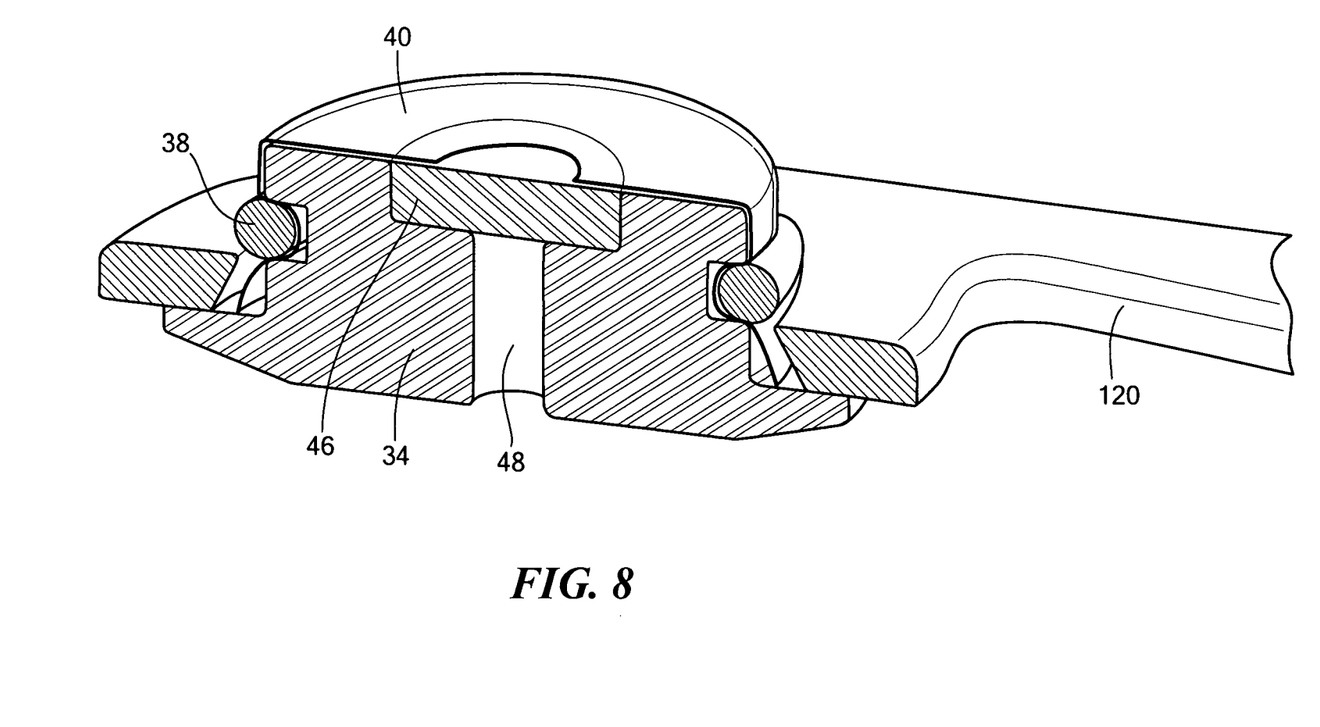
FIG. 8 is a schematic three dimensional cross sectional view showing an example of a filter cartridge and filter cartridge holder in accordance with an example of the invention.

FIG. 8 shows another example of a filter cartridge where polycarbonate membrane 40 is held in place over a well filled with felt filter 46 in filter holder 34. Filter insertion and removal tool 120 is also shown. Without felt filter 46, once the filter 36 becomes caked with particles, the pressure rise flattens out as more oil is pumped rendering any particle quantification based on pressure increases impossible. With felt filter 46 which traps particles pushed through a caked polycarbonate filter 36 after caking, the pressure continues to rise as more oil is pumped through the filter cartridge allowing for particle quantification over a longer period of time and over a greater volume of oil.

The result, in some embodiments, is a portable self contained device that allows for easy loading and unloading of the filter cartridge. Waste oil is collected typically in an absorbent filled bladder which requires no venting or pressure compensation if transported via airplane. Filter cartridges are fairly inexpensive and rebuildable. The collection area of the particles can be changed by changing the aperture area of the filter. The sample volume required (e.g., 3 ml) is fairly small compared to other devices. The preferred materials used in the filter cartridge do not interfere with x-ray measurements and O-ring 38, FIG. 8 holds filter membrane 36 in place on substrate 34 for low cost and ease of rebuilding. The preferred syringe is a 3 ml syringe clamped to the top of the filter membrane and sealed with respect thereto via an O-ring. The polycarbonate membrane filter typically may have 5 um in diameter by 10 um deep pores for measuring particles greater than 4-5 um.

One preferred system is a stand alone particle quantifier. In another example, the quantifier is a component or subsystem of an integrated sample analysis system such as that disclosed in patent application Ser. No. 13/374,937 filed Jan. 24, 2012 and incorporated herein by this reference.

Thus, although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A particle quantifier comprising:
   a filter system with at least a first filter having a predetermined number of pores of a first predetermined size;
   a pump;
   a fluid path from the pump to the filter system;
   a pressure sensor responsive to fluid pressure in the fluid path; and
   a processing module responsive to the pressure sensor and configured to:
      determine the pressure increase of a sample fluid in the fluid path as it is pumped through the filter system and particles in the fluid are trapped by the first filter,
      compare the determined pressure increase with calibration data, and
      based on the calibration data, estimate the concentration of particles greater than a second predetermined size present in the sample.

2. The particle quantifier of claim 1 in which the first predetermined size is less than the second predetermined size.

3. The particle quantifier of claim 1 in which the filter system includes a removable cartridge including the first filter.

4. The particle quantifier of claim 3 in which the removable cartridge includes a well in a filter holder, the first filter is a membrane filter disposed over the well, and the well includes a second filter having pores smaller than the pores of the membrane filter.

5. The particle quantifier of claim 1 in which the fluid path includes a syringe and the pump includes a motor driven plunger received in the syringe.

6. The particle quantifier of claim 5 in which the fluid path further includes a holder receiving the syringe and sealed with respect to the first filter.

7. The particle quantifier of claim 6 in which the pressure sensor is disposed to measure an internal pressure of the holder.

8. The particle quantifier of claim 1 in which the calibration data includes the pressure increase of a plurality of calibration fluid samples each with a known concentration of particles of a known size driven by the pump through the filter system.

9. The particle quantifier of claim 8 in which the calibration data further includes a calibration curve based on the pressure increase of said plurality of calibration fluid samples.

10. The particle quantifier of claim 9 in which the processing module is configured to determine first and second pressures at different times as the sample fluid is pumped through the filter system.

11. The particle quantifier of claim 1 in which the processing module is further configured to control the pump.

12. The particle quantifier of claim 11 in which the pump is a variable speed pump and the processing module is further configured to control the speed of the pump.

13. The particle quantifier of claim 12 in which the calibration data includes a first predetermined pressure and the processing module is configured to control and vary the speed of the pump so the sample fluid reaches said first predetermined pressure at a certain speed and to thereafter to hold said speed constant.

14. The particle quantifier of claim 11 in which the processing module is further configured to stop the pump if a predetermined maximum pressure is reached.

15. The particle quantifier of claim 14 in which the processing module is further configured to extrapolate a pressure increase for a predetermined volume of fluid pumped through the filter system after the pump is stopped.

16. The particle quantifier of claim 1 further including a second filter system with a third filter having a predetermined number of pores of a third predetermined size.

17. The particle quantifier of claim 16 in which the processing module is configured, based on the calibration data, to estimate the concentration of particles greater than a fourth predetermined size present in the sample.

18. The particle quantifier of claim 17 in which the third predetermined size is less than the fourth predetermined size and the third predetermined size is greater than the second predetermined size.

19. The particle quantifier of claim 1 in which the fluid path is portable.

20. The particle quantifier of claim 1 in which the particle quantifier is adapted to receive in place of the first filter a second filter having a predetermined number of pores of a third size, and in which the processing module is further configured to establish a differential measurement between different size particles in the sample fluid.

21. A particle quantifier comprising:
   a removable filter cartridge including a membrane filter disposed over a well in a filter holder, the filter membrane including a predetermined number of pores of a first predetermined size;
   a syringe;
   a pump with a motor driven plunger received in the syringe;

a syringe holder receiving the syringe therein;
a fluid path from the syringe to the filter;
a pressure sensor responsive to fluid pressure in the fluid path; and
a processing module, responsive to the pressure sensor and configured to:
   determine the pressure increase of a sample fluid in the fluid path as it is pumped from the syringe through the membrane filter and particles in the fluid are trapped by the pores of the membrane filter,
   compare the determined pressure increase with calibration data, and
   based on the calibration data, estimate the concentration of particles greater than a second predetermined size in the sample.

22. The particle quantifier of claim 21 in which the removable filter cartridge further includes a second filter under the membrane filter.

23. A particle quantifier comprising:
a filter system with at least a first filter having a predetermined number of pores of a predetermined size;
a pump;
a fluid path from the pump to the filter system;
a pressure sensor responsive to fluid pressure in the fluid path; and
a processing module responsive to the pressure sensor and configured to:
   determine the pressure increase of a sample fluid in the fluid path as it is pumped through the filter system and particles in the fluid are trapped by the first filter,
   compare the determined pressure increase with calibration data including the pressure increase of a plurality of calibration fluid samples each with a known concentration of particles of a known size driven by the pump through the first filter, and
   based on said calibration data, estimate the concentration of particles greater than a predetermined size present in the sample.

24. The particle quantifier of claim 23 in which the calibration data further includes a calibration curve based on the pressure increase of said plurality of calibration fluid samples.

25. The particle quantifier of claim 23 in which the processing module is configured to determine first and second pressures at different times as the sample fluid is pumped through the first filter.

26. A particle quantifier comprising:
at least a first filter with a predetermined number of pores of a predetermined size;
a variable speed pump;
a fluid path from the pump to the filter;
a pressure sensor responsive to fluid in the fluid path; and
a processing module responsive to the pressure sensor and configured to:
   control the pump and its speed,
   determine the pressure increase of a sample fluid in the fluid path as it is pumped by the pump through the filter and particles in the fluid are trapped by the filter,
   compare the determined pressure increase with calibration data, and
   based on the calibration data, estimate the concentration of particles greater than a second predetermined size present in the sample.

27. The particle quantifier of claim 26 in which the calibration data includes a first predetermined pressure and the processing module is configured to control the speed of the pump for a sample fluid to reach said first predetermined pressure in the fluid path.

28. The particle quantifier of claim 26 in which the processing module is further configured to stop the pump if a predetermined maximum pressure is reached.

29. The particle quantifier of claim 26 in which the fluid path is portable.

30. The particle quantifier of claim 26 in which the particle quantifier is adapted to receive in place of the first filter a second filter having a predetermined number of pores of a third size, and in which the processing module is further configured to establish a differential measurement between different size particles in the sample fluid.

31. A particle quantifier comprising:
a first filter with a predetermined number of pores of a first predetermined size;
a second filter with a predetermined number of pores of a second predetermined size;
a pump;
a fluid path from the pump to a filter;
a pressure sensor responsive to fluid in the fluid path; and
a processing module responsive to the pressure sensor and configured to:
   determine the pressure increase of a sample fluid in the fluid path as it is pumped through the filters and particles in the fluid are trapped by the filters,
   compare the determined pressure increase with calibration data, and
   based on the calibration data, estimate the concentration of particles between the first and second predetermined sizes present in the sample.

32. A particle quantification method comprising:
driving a sample fluid through a filter system with at least a first filter having a predetermined number of pores of a first predetermined size;
determining the pressure increase of the sample fluid as it is driven through the filter system;
comparing the determined pressure increase with calibration data representing the pressure increase of a plurality of calibration fluid samples as they were driven through one or more filters with the same or a similar predetermined number of pores of the first or a similar predetermined size; and
based on the comparison, estimating the concentration of particles present in the sample greater than a second predetermined size equal to or greater than the first predetermined size.

33. The method of claim 32 in which the calibration data includes the pressure increase of a plurality of calibration fluid samples each with a known concentration of particles of a known size driven through the filter system.

34. The method of claim 32 in which the calibration data further includes a calibration curve based on the pressure increase of said plurality of calibration fluid samples.

35. The method of claim 32 including determining first and second pressures at different times as the sample fluid is pumped through the filter system.

36. The method of claim 32 in which the calibration data includes a first predetermined pressure and the sample fluid is driven to reach said first predetermined pressure in the fluid path.

37. The method of claim 32 in which the driving stops if a predetermined maximum pressure is reached.

38. The method of claim 37 further including extrapolating the pressure increase for a predetermined volume of fluid pumped through the filter system after driving stops.

39. The method of claim 32 further including using a second filter with a predetermined number of pores of a third predetermined size.

40. The method of claim 39 further including in estimating the concentration of particles equal to or greater than the third predetermined size present in the sample.

* * * * *